United States Patent

Rentzea et al.

[11] 4,376,776
[45] Mar. 15, 1983

[54] DIBENZOFURAN DERIVATIVES AND THEIR USE FOR CONTROLLING FUNGI

[75] Inventors: Costin Rentzea, Heidelberg; Karl-Heinz Feuerherd; Bernd Zeeh, both of Ludwigshafen; Hubert Sauter, Mannheim; Ernst-Heinrich Pommer, Limburgerhof, all of Fed. Rep. of Germany

[73] Assignee: BASF Aktiengesellschaft, Fed. Rep. of Germany

[21] Appl. No.: 342,931

[22] Filed: Jan. 26, 1982

[30] Foreign Application Priority Data

Jan. 30, 1981 [DE] Fed. Rep. of Germany ....... 3103069

[51] Int. Cl.³ .................. A01N 43/12; C07D 307/91
[52] U.S. Cl. ................................ 424/267; 424/246; 424/248.52; 424/248.58; 424/274; 424/285; 546/133; 546/196; 544/60; 544/107; 548/454; 548/525; 549/460
[58] Field of Search .............. 549/460; 546/196, 133; 544/60, 107; 260/326.5 B, 326.5 S, 326.5 CA; 424/246, 248.52, 248.58, 267, 274, 285

[56] References Cited

U.S. PATENT DOCUMENTS 3,755,350 8/1973 Sauli ...................................... 424/273
4,327,214 4/1982 Rentzea et al. ....................... 546/133

OTHER PUBLICATIONS

Chem. Week, vol. 111 (1972), p. 39.
Pestic. Sci., vol. 10 (1979), pp. 393-398.

Primary Examiner—Henry R. Jiles
Assistant Examiner—Bernard Dentz
Attorney, Agent, or Firm—Keil & Witherspoon

[57] ABSTRACT

Dibenzofuran derivatives of the formula

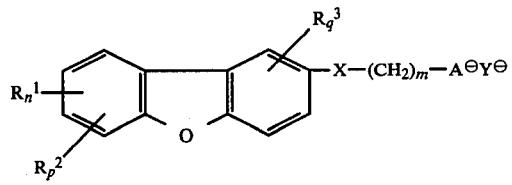

where $R^1$, $R^2$, $R^3$, X, A, Y, m, n, p and q have the meanings given in the description, and their use for controlling fungi.

7 Claims, No Drawings

DIBENZOFURAN DERIVATIVES AND THEIR USE FOR CONTROLLING FUNGI

The present invention relates to novel dibenzofuran derivatives, fungicides containing these compounds and a method of controlling fungi by means of these active ingredients.

The use of tetramethylthiuram disulfide as a fungicide has been disclosed in Chem. Week 111 (1972), 39. Other fungicides which are no less powerful than tetramethylthiuram disulfide against phytopathogenic fungi, eg. Botrytis cinerea, have also been disclosed eg. 2-aminobenzimidazolyl carbamate (R. Wegler, "Chemie der Pflanzenschutz-und Schä dlingsbekämpfungsmittel", Volume 4, page 180, Springer Verlag Berlin/ Heidelberg/New York, 1977) and 1-(isopropylcarbamamyl)-3-(3,5-dichlorophenyl)-imidazolidine-2,4-dione (German Laid-Open Application DOS 2,149,923). However, a very large number of phytopathogenic fungi rapidly become resistant to 2-aminobenzimidazolyl carbamate (loc.cit., pages 92–93 and 171–172), and 1-(isopropylcarbamyl)-3-(3,5-dichlorophenyl)-imidazolidine-2,4-dione spontaneously rearranges to inactive 1-(3,5-dichlorophenylcarbamyl)-3-isopropyl-imidazolidine-2,4-dione (Pestic. Sci., 10 (1979), 393).

We have found that dibenzofuran derivatives of the formula

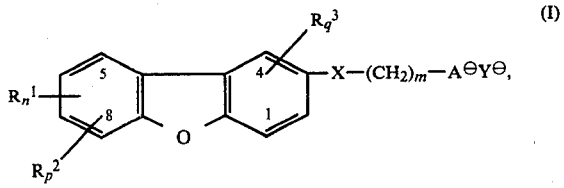

where $R^1$, $R^2$ and $R^3$ are identical or different and each is halogen, unsubstituted or halogen-substituted alkyl or alkoxy of 1 to 4 carbon atoms, cyano or nitro, n, p and q are 0, 1, 2 or 3, X is oxygen or sulfur, m is 2, 3 or 4, $A^{\oplus}$ is quinuclidinium or pyrrolizidinium, or $-N^{\oplus}R^4R^5R^6$, where $R^4$, $R^5$ and $R^6$ are identical or different and each independently of one another is alkyl, alkenyl or alkynyl of not more than 6 carbon atoms, cycloalkyl of not more than 12 carbon atoms or cycloalkenyl of not more than 7 carbon atoms, which as acyclic and cyclic radicals may be substituted by halogen, cyano, alkoxy of 1 to 4 carbon atoms or dialkylamino, where alkyl is of 1 to 4 carbon atoms, or is aralkyl which is unsubstituted or substituted by fluorine, chlorine, bromine, alkyl, alkenyl or alkoxy of not more than 4 carbon atoms, trifluoromethyl, nitro, cyano or alkoxycarbonyl of not more than 5 carbon atoms, or $R^5$ together with $R^6$ is part of a 5-, 6- or 7-membered heterocyclic ring which contains from 1 to 3 hetero-atoms and may be substituted by methyl or ethyl, and $Y^{\ominus}$ is the anion of any desired non-phytotoxic acid HY, have a more powerful fungicidal action than tetramethylthiuram disulfide.

Suitable substituents $R^1$, $R^2$ and $R^3$ in formula I include halogen, such as fluorine, chlorine, bromine and iodine, nitro, cyano and unsubstituted or halogen-substituted alkyl or alkoxy of 1 to 4 carbon atoms, such as methyl, ethyl, isopropyl, tert.-butyl, methoxy, ethoxy, trifluoromethyl, difluoromethoxy and tetrafluoroethoxy.

$A^{\oplus}$ in formula I is quinuclidinium or pyrrolizidinium, or $-N^{\oplus}R^4R^5R^6$. $R^4$, $R^5$ and $R^6$ in this formula are alkyl, alkenyl or alkynyl of not more than 6 carbon atoms, preferably of not more than 4 carbon atoms, which may be substituted by halogen, such as fluorine, chlorine or bromine, or by alkoxy of 1 to 4 carbon atoms, cyano or dialkylamino, where alkyl is of 1 to 4 carbon atoms, for example methyl, ethyl, n-propyl, isopropyl, n-butyl, isobutyl, n-pentyl, isopentyl, n-hexyl, allyl, but-2-enyl, 4-chloro-but-2-enyl, propargyl, trifluoromethyl, 2-chloroethyl and 2-bromoethyl, or are cycloalkyl of not more than 12 carbon atoms or cycloalkenyl of not more than 7 carbon atoms which may be substituted by halogen, such as fluorine, chlorine or bromine, alkoxy of 1 to 4 carbon atoms, cyano or dialkylamino, where alkyl is of 1 to 4 carbon atoms, for example cyclohexyl, 2-dimethylaminocyclohexyl and cyclododecyl; or aralkyl, such as benzyl, phenethyl or naphthylmethyl, which is unsubstituted or substituted by fluorine, chlorine, bromine, alkyl, alkenyl or alkoxy of not more than 4 carbon atoms, trifluoromethyl, nitro, cyano or alkoxycarbonyl of not more than 5 carbon atoms, for example 2-fluorobenzyl, 4-fluorobenzyl, 2-chlorobenzyl, 4-chlorobenzyl, 3-bromobenzyl, 4-bromobenzyl, 3-trifluoromethylbenzyl, 4-trifluoromethylbenzyl, 2-methylbenzl, 3-methylbenzyl, 4-methylbenzyl, 4-tert.-butylbenzyl, 4-nitrobenzyl, 2,4-dichlorobenzyl, 3,4-dichlorobenzyl, 2,4-dimethylbenzyl, 3,4-dimethylbenzyl, 4-methoxybenzyl and naphth-1-ylmethyl.

$R^5$ and $R^6$ can also form an alkylene group which, together with the quaternary nitrogen or which $R^5$ and $R^6$ are substituents, form a 5-, 6- or 7-membered heterocyclic ring which has from 1 to 3 hetero-atoms in the ring, for example a pyrrolidinium, piperidinium, hexamethyleneiminium, morpholinium or thiomorpholinium which is substituted by $R^4$ on the quaternary nitrogen. These rings may be substituted by methyl or ethyl.

Since the effect of the compounds of the formula I according to the invention is to be attributed to the cation, $Y^{\ominus}$ can be any desired anion from a non-phytotoxic acid, for example methylsulfonate, p-dodecylbenzenesulfonate, sulfate, methosulfate, nitrate, phosphate, iodide and especially chloride and bromide.

Compounds of the formula I where $R^1$ is halogen, such as fluorine, chlorine or bromine, straight-chain or branched alkyl or alkoxy of 1 to 4 carbon atoms, such as methyl, ethyl, isopropyl, tert.-butyl, methoxy or ethoxy, nitro or trifluoromethyl, p and q are 0, n is 1, 2 or 3, X is oxygen, m is 2, 3 or 4, $A^{\oplus}$ is $-N^{\oplus}R^4R^5R^6$ and $Y^{\ominus}$ is the anion of any desired non-phytotoxic acid HY are preferred.

$R^4$, $R^5$ and $R^6$ can be identical or different and each independently of one another is straight-chain or branched unsubstituted or halogen-substituted alkyl of 1 to 5 carbon atoms, such as methyl, ethyl, n-propyl, isopropyl, n-butyl, isobutyl, n-pentyl, isopentyl, 2-chloroethyl, 3-chloropropyl, 2-bromoethyl, 3-bromopropyl or 4-bromobutyl, alkenyl of 3 or 4 carbon atoms, such as allyl or but-2-enyl, or cycloalkyl of 3 to 6 carbon atoms, such as cyclopropyl or cyclohexyl.

In another group of preferred compounds, $R^4$ is benzyl which is unsubstituted or substituted by fluorine, chlorine, bromine, trifluoromethyl, nitro or alkyl of 1 to 4 carbon atoms, such as benzyl, 2-fluorobenzyl, 4- fluorobenzyl, 2-chlorobenzyl, 4-chlorobenzyl, 3-bromobenzyl, 4-bromobenzyl, 3-trifluoromethylbenzyl, 4-trifluoromethylbenzyl, 2-methylbenzyl, 3-methylbenzyl, 4-methylbenzyl, 4-tert.-butylbenzyl, 4-nitrobenzyl, 2,4-dichlorobenzyl, 3,4-nitrobenzyl, 2,4-dimethylbenzyl or 3,4-dimethylbenzyl, and R⁵ together with R⁶ is part of a 5-, 6- or 7-membered heterocyclic ring which has from 1 to 3 heteroatoms and may be substituted by methyl or ethyl, for example a pyrrolidinium, piperidinium, hexamethyleneiminium, morpholinium, thiomorpholinium, 2,6-dimethylmorpholinium, 2,6-dimethyl-thiomorpholinium, 2-ethyl-piperidinium or 4-methylpiperidinium ring.

Examples of dibenzofuran derivatives of the formula I are N-methyl-N-2-(7-bromodibenzofuran-3-oxy)-ethylpyrrolidinium bromide, N-methyl-N-2-(7-bromodibenzofuran-3-oxy)-ethylpiperidinium bromide, N-allyl-N-2-(7-bromodibenzofuran-3-oxy)-ethyl-(2',6'-dimethylmorpholinium) bromide, N-benzyl-N-2-(7-bromodibenzofuran-3-oxy)-ethylpyrrolidinium bromide, N-benzyl-N-2-(7-bromodibenzofuran-3-oxy)-ethylpiperidinium chloride, N-benzyl-N-4-(7-bromodibenzofuran-3-oxy)-butylpiperidinium chloride, N-methyl-N-4-(7-fluorodibenzofuran-3-oxy)-butylpiperidinium bromide, N-benzyl-N-2-(7-fluorodibenzofuran-3-oxy)-ethylpiperidinium chloride, N-methyl-N-2-(7-chlorodibenzofuran-3-oxy)-ethylpyrrolidium bromide, N-allyl-N-2-(7-chlorodibenzofuran-3-oxy)-ethylpyrrolidinium bromide, N-butyl-N-2-(7-chlorodibenzofuran-3-oxy)-ethylpyrrolidinium bromide, N-benzyl-N-2-(7-chlorodibenzofuran-3-oxy)-ethylpyrrolidinium chloride, N-allyl-N-3-(7-chlorodibenzofuran-3-oxy)-propylpiperidinium bromide, N-allyl-N-3-(7-chlorodibenzofuran-3-thio)-propylpiperidinium bromide, N-methyl-N-4-(7-chlorodibenzofuran-3-oxy)-butylpiperidinium bromide, N-benzyl-N-3-(7-chlorodibenzofuran-3-oxy)-propylpiperidinium bromide, N-4-(7-chlorodibenzofuran-3-oxy)-butylpyrrolizidinium bromide, N-(but-1'-en-2'-yl)-N-2-(7-chlorodibenzofuran-3-oxy)-ethylpiperidinium bromide, N-methyl-N-2-(7-chlorodibenzofuran-3-oxy)-ethylhexamethyleneimmonium bromide, N-propyl-N-2-(7-chlorodibenzofuran-3-oxy)-ethylhexamethyleneimmonium bromide, N-benzyl-N-2-(7-chlorodibenzofuran-3-oxy)-ethylhexamethyleneimmonium bromide, N,N,N-triethyl-N-2-(7-chlorodibenzofuran-3-oxy)-ethylammonium bromide, N,N-dimethyl-N-cyclohexyl-N-2-(7-chlorodibenzofuran-3-oxy)-ethylammonium bromide, N,N-dimethyl-N-(2'-dimethylamino)-cyclohexyl-N-2-(7-chlorodibenzofuran-3-oxy)-ethylammonium bromide, N,N-dimethyl-N-benzyl-N-2-(7-chlorodibenzofuran-3-oxy)-ethylammonium bromide, N-(4'-chloro-but-2'-en-1'-yl)-N-2-(7-chlorodibenzofuran-3-oxy)-ethylpiperidinium chloride, N-benzyl-N-2-(7-chlorodibenzofuran-3-oxy)-ethyl-(2',6'-dimethylmorpholinium) bromide, N-benzyl-N-2-(7-chlorodibenzofuran-3-oxy)-ethyl-(2',6'-dimethylthiomorpholinium) bromide, N-benzyl-N-2-(7-chlorodibenzofuran-3-oxy)-ethylpiperidinium chloride, N-(4'-fluorobenzyl)-N-2-(7-chlorodibenzofuran-3-oxy)-ethylpiperidinium bromide, N-(4'-chlorobenzyl)-N-2-(7-chlorodibenzofuran-3-oxy)-ethylpiperidinium chloride, N-(4'-methylbenzyl)-N-2-(7-chlorodibenzofuran-3-oxy)-ethylpiperidinium bromide, N-(4'-nitrobenzyl)-N-2-(7-chlorodibenzofuran-3-oxy)-ethylpiperidinium bromide, N-(4'-trifluoromethyl-benzyl)-N-2-(7-chlorodibenzofuran-3-oxy)-ethylpiperidinium bromide, N-(4'-tert.-butylbenzyl)-N-2-(7-chlorodibenzofuran-3-oxy)-ethylpiperidinium bromide, N-(naphth-1-ylmethyl)-N-2-(7-chlorodibenzofuran-3-oxy)-ethylpiperidinium chloride, N-benzyl-N-2-(7-chlorodibenzofuran-3-oxy)-ethyl-(4'-methylpiperidinium) chloride, N-(3,4-dimethylbenzyl)-N-2-(7-chlorodibenzofuran-3-oxy)-ethyl-(4'-methylpiperidinium) chloride, N-benzyl-N-2-(7-chlorodibenzofuran-3-oxy)-ethyl-(2'-ethylpiperidinium) bromide, N,N-dimethyl-N-cyclodecyl-N-2-(6-trifluoromethyl-dibenzofuran-3-oxy)-ethylammonium bromide and N-methyl-N-4-(6,8-dichloro-7-methyldibenzofuran-3-oxy)-butylpiperidinium bromide.

The dibenzofuran derivatives of the formula I are obtained by reacting
(a) a compound of the formula

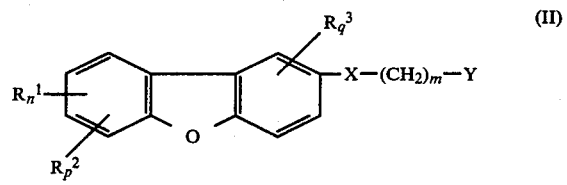

where R¹, R², R³, X, Y, m, n, p and q have the above meanings, with a tertiary amine of the formula A having the above meanings, or
(b) a compound of the formula

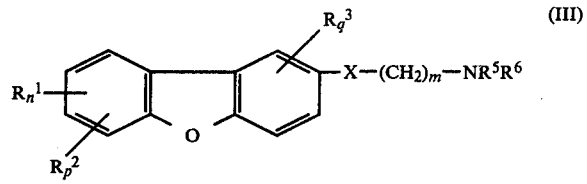

where R¹, R², R³, R⁵, R⁶, X, m, n, p and q have the above meanings, with a compound of the formula

R⁴-Y  (IV)

where R⁴ and Y have the above meanings.

Reactions (a) and (b) are carried out in the presence or absence of a solvent or diluent at from 20° to 150° C., preferably from 30° to 140° C. Advantageously, the starting substance of the formula II is reacted with a 2-fold to 10-fold molar excess of the amine of the formula A.

Examples of preferred solvents or diluents which are inert toward the reactants are aliphatic or aromatic hydrocarbons or halohydrocarbons, such as pentane, cyclohexane, benzene, toluene, xylene, chlorobenzene and the dichlorobenzenes, aliphatic ketones, such as acetone, methyl ethyl ketone, diethyl ketone and cyclopentanone, ethers, such as diethyl ether, dimethoxyethane, tetrahydrofuran and dioxane, esters, such as ethyl acetate, nitriles, such as acetonitrile, and amides, such as dimethylformamide, dimethylacetamide and N-methylpyrrolidone, and mixtures of these solvents.

The starting substances of the formula II can be easily prepared by a conventional process, for example by etherifying a dibenzofuran-3ol or a dibenzofuran-3-thiol with an aliphatic dihalide, such as 1,2-dibromoethane, 1,3-dichloropropane, 1-chloro-3-bromopropane, 1,3-dibromopropane, 1-chloro-4-bromobutane or 1,4-dibromobutane, preferably in boiling methyl ethyl ketone, diethyl ketone or cyclopentanone in the presence of not less than an equivalent amount of sodium carbonate or potassium carbonate (Houben-Weyl, Methoden der Organischen Chemie, Volume 6/3, pages 54–59, Georg Thieme-Verlag, Stuttgart, 1965). Alternatively, a dibenzofuran-3-oxyalkanol can be reacted with thionyl chloride or with phosphorus tribromide to give a compound of the formula II (Rec. Trav. Chim. 76 (1957), 129–146).

Examples of tertiary amines of the formula A which can be used are trimethylamine, triethylamine, tripropylamine, methyl-diethylamine, methyl-dipropylamine, tributylamine, tripentylamine, 1,2-bis-(dimethylamino)-cyclohexane, N,N-dimethyl-N-cyclododecylamine, N,N-dimethyl-N-cyclohexylamine, N,N-dimethyl-N-benzylamine, N-methylpyrrolidine, N-ethylpyrrolidine, N-allylpyrrolidine, N-propylpyrrolidine, N-butylpyrrolidine, N-methylpiperidine, N-2-dimethylpiperidine, N-3-dimethylpiperidine, N,N-dimethylpiperidine, N-2,4-trimethylpiperidine, N-3,5-trimethylpiperidine, N-2,5-trimethylpiperidine, N-methyl-2-ethylpiperidine, N-ethylpiperidine, N-methyl-3-hydroxymethylpiperidine, N-methylmorpholine, N-ethylmorpholine, N-2,6-trimethylmorpholine, N-ethyl-2,6-dimethylmorpholine, N-methyl-hexamethyleneimine, N-propyl-hexamethyleneimine, quinuclidine and pyrrolizidine.

The tertiary amines of the formula III can be prepared by a conventional process, for example in accordance with the equation

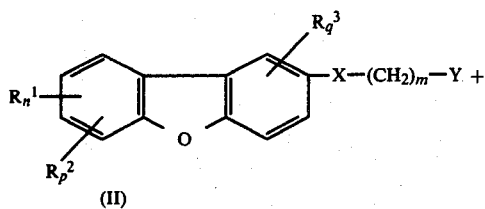
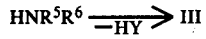

by alkylating a secondary amine of the formula $HNR^5R^6$, where $R^5$ and $R^6$ have the above meanings, with a compound of the formula II. The reaction conditions here correspond to those for reaction (a).

The acid HY formed in the reaction can easily be removed, for example by treating the reaction mixture with an aqueous alkali metal hydroxide solution.

Examples of suitable amines of the formula $HNR^5R^6$ are dimethylamine, dipropylamine, diisopropylamine, diallylamine, dibutylamine, diisobutylamine, N-methylbenzylamine, pyrrolidine, piperidine, 2-methylpiperidine, 3-methylpiperidine, 4-methylpiperidine, 2,4-dimethylpiperidine, 3,5-dimethylpiperidine, 2,6-dimethylpiperidine, 2-ethylpiperidine, N-ethylbenzylamine, N-butylbenzylamine, morpholine, 2-methylmorpholine, 3-methylmorpholine, 2,6-dimethylmorpholine, 2,5-dimethylmorpholine, 2,6-dimethylthiomorpholine and hexamethyleneimine.

Examples of compounds of the formula IV which can be used are methyl chloride, methyl bromide, methyl iodide, dimethyl sulfate, ethyl chloride, ethyl bromide, ethyl iodide, diethyl sulfate, dibromoethane, 2-methoxyethyl bromide, propyl bromide, propyl iodide, 1-chloro-3-bromopropane, 1,3-dibromopropane, isopropyl bromide, allyl chloride, allyl bromide, n-butyl bromide, butyl chloride, 1,4-dibromobutane, 1,4-dichlorobutane, propargyl chloride, propargyl bromide, 1-bromobut-2-ene, 1,4-dichlorobut-2-ene, benzyl chloride, benzyl bromide, 2-fluorobenzyl chloride, 3-fluorobenzyl bromide, 4-fluorobenzyl bromide, 2-chlorobenzyl chloride, 3-chlorobenzyl bromide, 4-chlorobenzyl bromide, 4-bromobenzyl bromide, 2,4-dichlorobenzyl chloride, 3,4-dichlorobenzyl chloride, 4-methylbenzyl bromide, 2,4-dimethylbenzyl bromide, 3-trifluoromethylbenzyl chloride, 4-trifluoromethylbenzyl bromide, 4-nitrobenzyl chloride, 4-nitrobenzyl bromide, 4-tert.-butylbenzyl bromide, 3,4,5-trimethoxybenzyl chloride, 4-cyanobenzyl chloride and 1-chloromethylnaphthalene.

The following dibenzofuran-3-ols and dibenzofuran-3-thiols, for example, can be used for the preparation of starting compounds of the formulae II and III: dibenzofuran-3-ol, dibenzofuran-3-thiol, 7-fluorodibenzofuran-3-ol, 7-chlorodibenzofuran-3-ol, 7-chlorodibenzofuran-3-thiol, 2,4,7-trichlorodibenzofuran-3-5-chlorodibenzofuran-3-ol, 6-chlorodibenzofuran-3-ol, 8-chlorodibenzofuran-3-ol, 5,7-dichlorobenzofuran-3-ol, 6,7-dichlorodibenzofuran-3-ol, 7,8-dichlorodibenzofuran-3-ol, 7-bromodibenzofuran-3-ol, 7-bromodibenzofuran-3-thiol, 7-methyldibenzofuran-3-ol, 6.8-dichloro-7-methyldibenzofuran-3-ol, 6-trifluoromethyldibenzofuran-3-ol, 7-trifluoromethyldibenzofuran-3-ol, 7-trifluoromethyldibenzofuran-3-thiol, 7-tert.-butyldibenzofuran-3-ol, 7-methoxydibenzofuran-3-ol, 7-chloro-2-nitrodibenzofuran-3-ol and 7-ethoxydibenzofuran-3-ol.

The Examples which follow illustrate the preparation of the compounds of the formula I.

EXAMPLE 1

83 g (0.6 mole) of potassium carbonate were added to a solution of 262 g (1.2 moles) of 7-chlorodibenzofuran-3-ol in 600 ml of dry dimethylformamide, and a solution of 212 g (2.55 moles) of ethylene carbonate in 300 ml of dimethylformamide was then added dropwise at 100° C. in the course of 90 minutes. The mixture was stirred at 120° C. for 8 hours and filtered off with suction at 100° C., and the filtrate was concentrated. The residue was dissolved in 2.5 l of ethyl acetate, the solution was washed three times with 300 ml of water each time, the organic layer was dried, decolorized with 10 g of animal charcoal and concentrated to 500 ml and the concentrate was cooled to 10° C. The precipitate was filtered off with suction and washed, at +5° C., with 60 ml of methanol, 50 ml of ether and 200 ml of petroleum ether in succession, and dried. 225 g of 2-(7-chlorodibenzofuran-3-oxy)-ethanol of melting point 118°–120° C. were obtained; yield: 71.4% of theory.

11.9 g (0.15 mole) of pyridine were added to a suspension of 26.2 g (0.1 mole) of 2-(7-chlorodibenzofuran-3-oxy)-ethanol in 100 ml of dry toluene, and 17.9 g (0.15 mole) of thionyl chloride were then added dropwise at 3°–15° C. The mixture was stirred for 1 day at 40° C. and for a further 8 hours at 70° C. and cooled, and 150 ml of toluene and 200 ml of ice-water were added. The organic layer was washed with 100 ml of water, 50 ml of hydrochloric acid and 50 ml of 1 N sodium hydroxide solution in succession and finally with 100 ml of water, and was dried and concentrated. The solid residue was stirred with 40 ml of petroleum ether at +3° C. (icebath) for 30 minutes, filtered off with suction, washed with a little cold petroleum ether and dried. 22.8 g of 1-chloro-2-(7-chlorodibenzofuran-3-oxy)-ethane were obtained as colorless crystals of melting point 105°–107° C.; yield: 81% of theory.

70.2 g (0.25 mole) of 1-chloro-2-(7-chlorodibenzofuran-3-oxy)-ethane and 150 g (1.76 moles) of piperidine were stirred for 8 hours at 100° C. and for a further 8 hours at 140° C. and cooled, and the mixture was then concentrated under reduced pressure. The residue was partitioned between 100 ml of water and 400 ml of ether, and 100 ml of 50% strength sodium hydroxide solution were added, while cooling with ice. The ether layer was separated off, washed with 100 ml of water, dried and concentrated under reduced pressure. The solid residue was stirred with 50 ml of n-pentane at +5° C. for 30 minutes, filtered off with suction and washed with 30 ml of cold pentane. 70 g of N-2-(7-chlorodibenzofuran-3-oxy)-ethylpiperidine were obtained as colorless crystals of melting point 65°–67° C.; yield: 84% of theory.

A solution of 11.5 g (0.035 mole) of N-2-(7-chlorodibenzofuran-3-oxy)-ethylpiperidine and 6.1 g (0.05 mole) of allyl bromide in 30 ml of dry dioxane and 30 ml of dry acetonitrile was stirred at 80° C. for 8 hours and cooled to 0° C. The crystalline precipitate was filtered off with suction, washed with 50 ml of dry ether and dried under reduced pressure. 13.5 g of N-allyl-N-2-(7-chlorodibenzofuran-3-oxy)-ethylpiperidinium bromide were obtained as white crystals of melting point 189°–191° C.; yield: 85.6% of theory (Compound No. 1).

EXAMPLE 2

A mixture of 98.4 g (0.45 mole) of 7-chlorodibenzofuran-3-ol, 200 ml of methyl ethyl ketone, 93 g (0.67 mole) of potassium carbonate and 283 g (1.4 moles) of dibromopropane was refluxed for 24 hours. The inorganic precipitate was filtered off with suction and the filtrate was concentrated under reduced pressure. The residue was dissolved in 500 ml of methylene chloride and the solution was washed with 100 ml of water, 100 ml of 2 N sodium hydroxide solution and 100 ml of water in succession, dried over sodium sulfate and concentrated under reduced pressure. The solid residue was left to stand with 30 ml of pentane at 0° C. for 30 minutes, filtered off with suction and washed with 30 ml of cold n-pentane. 77 g of pure 1-bromo-3-(7-chlorodibenzofuran-3-oxy)-propane of melting point 83°–85° C. were obtained; yield: 50% of theory.

A solution of 14 g (0.041 mole) of 1-bromo-3-(7-chlorodibenzofuran-3-oxy)-propane and 4.8 g (0.048 mole) of N-methylpiperidine in 40 ml of dioxane and 40 ml of acetonitrile was stirred at 70° C. for 8 hours. The solution was cooled to +10° C. and the crystalline precipitate formed was filtered off with suction, washed with 30 ml of ether and finally with 50 ml of n-pentane and dried. 13.4 g of N-methyl-N-3-(7-chlorodibenzofuran-3-oxy)-propylpiperidinium bromide of melting point 212°–215° C. were obtained; yield: 74% of theory (Compound No. 2).

The following compounds of the formula I, for example, were prepared in a manner similar to that in Examples 1 and 2:

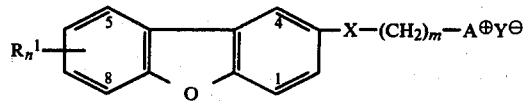

| No. | $R_n^1$ | m | X | $A^\oplus$ | $Y^\ominus$ | M.p.[°C.] |
|---|---|---|---|---|---|---|
| 3 | H | 2 | O | 1-Methyl-pyrrolidinium | $Br^\ominus$ | 158–160 |
| 4 | " | 2 | " | 1-Ethyl-pyrrolidinium | " | 149–150 |
| 5 | " | 2 | " | 1-Allyl-pyrrolidinium | " | 152–154 |
| 6 | " | 2 | " | 1-n-Propyl-pyrrolidinium | " | 197–199 |
| 7 | " | 2 | " | 1-Methyl-piperidinium | " | 191–193 |
| 8 | " | 2 | " | 1-Allyl-piperidinium | " | 168–170 |
| 9 | 7-F | 2 | " | 1-Methyl-piperidinium | " | 144–146 |
| 10 | 6-Cl | 2 | " | 1-Methyl-pyrrolidinium | " | 191–192 |
| 11 | " | 2 | " | 1-Methyl-piperidinium | " | 173–175 |
| 12 | " | 2 | " | N,N—Dimethyl-N—(2-dimethylamino)-cyclohexylammonium | " | 244–246 |
| 13 | 6-Br | 2 | " | 1-Methyl-pyrrolidinium | " | 181–183 |
| 14 | 7-Br | 2 | " | 1-Methyl-piperidinium | " | 217–219 |
| 15 | " | 2 | " | 1-Allyl-2,6-dimethyl-morpholinium | " | 201–203 |
| 16 | 6-$CF_3$ | 2 | " | 1-Methyl-pyrrolidinium | " | 218–220 |
| 17 | " | 2 | " | 1-Methyl-piperidinium | " | 192–194 |
| 18 | " | 2 | " | N,N—Dimethyl-amino)-cyclohexyl-ammonium | " | 198–200 |
| 19 | " | 2 | " | N,N—Dimethyl-N—cyclododecylammonium | " | 209–213 |
| 20 | 7-Cl | 2 | " | 1-Methyl-pyrrolidinium | " | resin |
| 21 | " | 2 | " | 1-Allyl-pyrrolidinium | " | 152–154 |
| 22 | " | 2 | " | 1-n-Butyl-pyrrolidinium | " | 212–214 |
| 23 | " | 3 | " | 1-Methyl-pyrrolidinium | " | 154–157 |
| 24 | " | 3 | " | 1-n-Butyl-pyrrolidinium | " | 192–195 |
| 25 | " | 4 | " | 1-Methyl-pyrrolidinium | " | 165–167 |
| 26 | " | 4 | " | 1-n-Butyl-pyrrolidinium | " | 189–191 |
| 27 | " | 3 | " | 1-Allyl-piperidinium | " | 191–192 |
| 28 | " | 3 | S | 1-Allyl-piperidinium | " | 172–174 |
| 29 | " | 4 | O | 1-Methyl-piperidinium | " | 168–169 |
| 30 | " | 4 | " | 1-Allyl-piperidinium | " | 154–156 |
| 31 | " | 4 | " | Pyrrolizidinium | " | 144–147 |
| 32 | " | 3 | " | N,N—Dimethyl-N—(2-dimethylamino)-cyclohexylammonium | " | 182–184 |
| 33 | " | 2 | " | 1-(2'-Buten-1'-yl)-piperidinium | " | 197–199 |
| 34 | " | 2 | " | 1-Benzyl-2,6-dimethyl-morpholinium | " | 169–171 |
| 35 | " | 2 | " | 1-Benzyl-2,6-dimethyl-thiomorpholinium | " | 150–152 |
| 36 | " | 2 | " | 1-Methyl-hexamethylen-iminium | " | 198–200 |
| 37 | " | 2 | " | 1-n-Propyl-hexamethyleniminium | " | 217–219 |
| 38 | " | 2 | " | N,N,N—Triethyl-ammonium | " | 197–199 |
| 39 | " | 2 | " | N,N—Dimethyl-N—cyclohexylammonium | $Br^\oplus$ | 143–145 |
| 40 | " | 2 | " | N,N—Dimethyl-N—(2-dimethylamino)-cyclohexyl-ammonium | " | resin |
| 41 | " | 2 | " | N,N—Dimethyl-N—benzylammonium | " | 193–195 |
| 42 | " | 2 | " | 1-Benzyl-piperidinium | $Cl^\ominus$ | 201–203 |
| 43 | " | 2 | " | 1-(4'-Fluorobenzyl)-piperidinium | $Br^\ominus$ | 209–211 |
| 44 | " | 2 | " | 1-(3'-Methylbenzyl)-piperidinium | " | 202–204 |
| 45 | " | 2 | " | 1-(2',4'-Dichlorobenzyl)-piperidinium | $Cl^\ominus$ | 181–183 |
| 46 | " | 2 | " | 1-(4'-Chlorobenzyl)-piperidinium | " | 185–186 |
| 47 | " | 2 | " | 1-(4'-Nitrobenzyl)-piperidinium | $Br^\ominus$ | 136–138 |
| 48 | " | 2 | " | 1-(4'-Trifluoromethyl-benzyl)-piperidinium | " | 208–210 |
| 49 | " | 2 | " | 1-(4'-tert.-Butylbenzyl)-piperidinium | " | 204–206 |
| 50 | " | 2 | " | 1-(1'-Naphthylmethyl)-piperidinium | $Cl^\ominus$ | 176–177 |
| 51 | " | 2 | " | 1-(4'-Chloro-2'-buten-1'-yl)-piperidinium | " | resin |

-continued

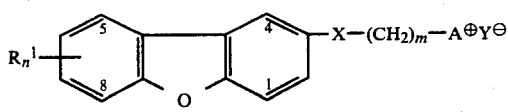

| No. | $R_n^1$ | m | X | $A^\oplus$ | $Y^\ominus$ | M.p.[°C.] |
|---|---|---|---|---|---|---|
| 52 | " | 2 | " | 1-Benzyl-4-methyl-piperidinium | " | 193–195 |
| 53 | " | 2 | " | 1-Benzyl-2-ethylpiperidinium | $Br^\ominus$ | 157–159 |
| 54 | " | 2 | " | 1-(1'-Naphthylmethyl)-4-methylpiperidinium | $Cl^\ominus$ | 165–168 |

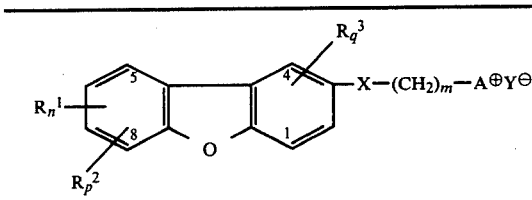

| No. | $R_n^1$ | | m | X | $A^\oplus$ | $Y^\ominus$ | M.p.[°C.] |
|---|---|---|---|---|---|---|---|
| 55 | 6-Cl | 7-Cl | 2 | O | 1-Methyl-pyrrolidinium | $Br^\ominus$ | 199–201 |
| 56 | " | " | 2 | " | 1-Methyl-pyrrolidinium | " | 211–213 |
| 57 | " | " | 2 | " | 1-Methyl-pyrrolidinium | " | 116–168 |
| 58 | 5-Cl | " | 2 | " | 1-Methyl-pyrrolidinium | " | 119–121 |
| 59 | " | " | 2 | " | 1-Methyl-pyrrolidinium | " | 227–229 |
| 60 | 6-Cl, 8-Cl | 7-CH$_3$ | 4 | " | 1-Methyl-piperidinium | " | 245–247 |
| 61 | 7-Cl | | 2 | " | 1-(3',4'-Dichlorobenzyl)-piperidinium | $Cl^\ominus$ | 202–204 |
| 62 | " | | 2 | " | 1-(2',4'-Dichlorobenzyl)-hexamethyleniminium | " | 186–188 |

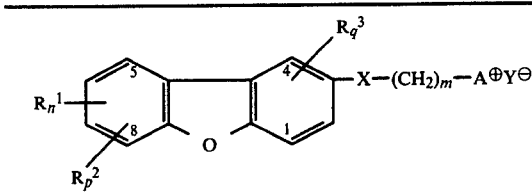

| No. | $R_n^1$ | m | X | $A^\oplus$ | $Y^\ominus$ | M.p.[°C.] |
|---|---|---|---|---|---|---|
| 63 | 7-Cl | 2 | O | 1-(2',4'-Dichlorobenzyl)-2-ethylpiperidinium | $Cl^\ominus$ | 149–152 |
| 64 | " | 2 | " | 1-(2',4'-Dichlorobenzyl)-4-methylpiperidinium | " | 185–187 |
| 65 | " | 2 | " | 1-(4'-Bromobenzyl)-piperidinium | " | 210–212 |
| 66 | " | 2 | " | 1-(2'-Chloro-4'-nitrobenzyl)-piperidinium | " | 202–204 |
| 67 | " | 2 | " | N—Methyl-N—benzyl-N—(4'-tert.-butylbenzyl)-ammonium | " | 153–155 |
| 68 | " | 2 | " | 1-(4'-tert.-Butylbenzyl)-hexamethyleniminium | " | 135–137 |
| 69 | " | 2 | " | 1-(4'-tert.-Butylbenzyl)-4-methylpiperidinium | " | 195–197 |
| 70 | " | 2 | " | 1-(4'-tert.-Butylbenzyl)-2,6-dimethylmorpholinium | " | 135–138 |
| 71 | " | 3 | " | 1-(4'-tert.-Butylbenzyl)-piperidinium | " | 225–227 |

The novel active ingredients have a strong fungitoxic action on phytopathogenic fungi. They are particularly suitable for preventing and curing plant diseases caused by microorganisms such as Botrytis begonie, Botrytis cinerea, Plasmopara viticola, Monilia fructigena, Alternaria solani, Sclerotinia sclerotiorum, Piricularia oryzae, Pellicularia filamentosa, Erysiphe graminis, Erysiphe cichoriacearum, Chaetomium globosum, Sclerotinia cinerea, Aspergillus niger, Xanthomonas oryzae, and Xanthomonas citri.

The active ingredients according to the invention may simultaneously suppress the growth of two or more of the abovementioned fungi, and they are very well tolerated by plants. Some of the active ingredients have curative properties, i.e., the agents may also be applied after the plants have been infected by the pathogen, and success is still ensured.

The fungicidal agents contain from 0.1 to 95, and preferably from 0.5 to 90, wt% of active ingredient. The application rates depend on the type of effect desired, and are from 0.1 to 5 kg of active ingredient per hectare.

The agents according to the invention may also be mixed and applied with other active ingredients, e.g., herbicides, insecticides, growth regulators, other fungicides and fertilizers. When mixed with other fungicides, the spectrum of fungicidal action is in many cases increased; with a number of these fungicidal compositions, synergistic effects also occur; i.e., the fungicidal action of the combination product is greater than the effect of the individual components added together. The spectrum of action is particularly favorably influenced when the compounds according to the invention are mixed with the following fungicides: manganese N,N-ethylene-bis-dithiocarbamate, manganese zinc N,N-ethylenediamine-bis-dithiocarbamate, the ammonia complex of zinc N,N-ethylene-bis-dithiocarbamate and N,N'-polyethylene-bis(thiocarbamoyl)-disulfide, N-trichloromethylthiotetrahydrophthalimide, N-trichloromethylphthalimide, 5-ethoxy-3-trichloromethyl-1,2,3-thiadiazole, 2-methoxycarbonylaminobenzimidazole, 2-thiocyanomethylthiobenzothiazole, 1,4-dichloro-2,5-dimethoxybenzene, 2,3-dichloro-6-methyl-1,4-oxathiin-5-carboxylic acid anilide, 2-methyl-5,6-dihydro-4H-pyran-3-carboxylic acid anilide, 2,4,5-trimethylfuran-3-carboxylic acid anilide, 2-methylfuran-3-carboxylic acid anilide, 2,5-dimethylfuran-3-carboxylic acid cyclohexylamide, N-cyclohexyl-N-methoxy-2,5-dimethylfuran-3-carboxylic acid amide, 5-methyl-5-vinyl-3-(3,5-dichlorophenyl)-2,4-dioxo-1,3-oxazolidine, and 3-(3,5-dichlorophenyl)-5-methyl-5-methoxymethyl)-1,3-oxazolidine-2,4-dione.

However, the compounds according to the invention may also be combined with the following fungicides: dithiocarbamates and their derivatives, e.g. iron(III) dimethyldithiocarbamate, zinc dimethyldithiocarbamate, zinc N,N-ethylene-bis-dithiocarbamate, tetramethylthiuram disulfide, zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitro derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 2,3-dicyano-1,4-dithiaanthraquinone, 2-thio-1,3-dithio(4,5-b)-quinoxaline, methyl 1-(butylcarbamoyl)-2-benzimidazole-carbamate, 4-(2-chlorophenylhydrazono)-3-methyl-5-isoxazolone, pyridine-2-thio-1-oxide, 8-hydroxyquinoline and its copper salt, 2,3-dihydro-5-carboxanilido-6-methyl-1,4-oxathiin-4,4-dioxide, 2,3-dihydro-5-carboxanildio-6-methyl-1,4-oxathiin, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2-methyl-benzoic acid anilide, 2-iodo-benzoic acid anilide, 1-(3,4-dichloroanilino)-1-formylamino-2,2,2-trichloroethane, 2,6-dimethyl-N-tridecylmorpholine and its salts, 2,6-dimethyl-N-cyclododecyl-morpholine and its salts, α-(2-chlorophenyl-α-(4-chlorophenyl)-5-pyrimidine-methanol, 1-(4-chlorophenoxy)-3,3-dimethyl-1-(1H-1,2,4-triazol-1-yl)-2-butanone, and 1-(4-chlorophenoxy)-3,3-dimethyl-1-(1H-1,2,4-triazol-1-yl)-2-butanol.

The new active ingredients are applied for instance in the form of directly sprayable solutions, powders, suspensions (including high-percentage aqueous, oily or other suspensions or dispersions), emulsions, oil dispersions, pastes, dusts, broadcasting agents, or granules by spraying, atomizing, dusting, broadcasting or watering. The forms of application depend entirely on the purpose for which the agents are being used; at all events, they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, andureas, and vegetable products such as grain flours, bark meal, wood meal, and nutshell meal, cellulosic powders, etc.

Examples of such formulations are given below:

I. 90 parts by weight of the compound of Example 1 is mixed with 10 parts by weight of N-methyl-α-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 13 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 14 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 19 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 5 parts by weight of compound no. 25 is intimately mixed with 95 parts by weight of particulate kaolin. A dust is obtained containing 5% by weight of the active ingredient.

VII. 30 parts by weight of compound no. 37 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 42 is intimately mixed with 10 parts of the sodium salt of a phenolsulfonic acid-urea-formaldehyde condensate, 2 parts of silica gel and 48 parts of water to give a stable, aqueous dispersion.

IX. 20 parts of compound no. 51 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The following examples demonstrate the biological action of the new compounds. The agent used for comparison purposes was the prior art active ingredient tetramethylthiuram disulfide (Chem. Week, 111 (4), 39, 1972) known to be particularly suitable for combating Botrytis.

EXAMPLE A

Action on Botrytis cinerea in pimientos

Pimiento seedlings of the "Neusiedler Ideal Elite" variety were sprayed, after 4 to 5 leaves were well developed, to runoff with 0.025 wt% aqueous liquors containing (dry basis) 80% of active ingredient and 20% of sodium ligninsulfonate. After the sprayed-on layer had dried, the plants were sprinkled with a conidial suspension of the fungus Botrytis cinerea, and placed at 22° to 24° C. in a chamber of high humidity to obtain optimum conditions for promoting fungus growth. After 5 days, the disease had spread to such a great extent on the untreated plants that the necroses covered the major portion of the leaves.

In this test, active ingredients nos. 1, 2, 13, 14, 15, 16, 20, 22, 23, 25, 27, 29, 31, 32, 33, 36, 37, 38, 40, 41, 42, 45, 58 and 60 had a better action than the comparative agent.

EXAMPLE B

Action on cucumber mildew

Leaves of pot-grown cucumber seedlings were sprayed with aqueous emulsions, the solids comprising 80% of active ingredient and 20% of emulsifier, and dusted, after the sprayed-on layer had dried, with spores of cucumber mildew (Erysiphe cichoriacearum). The plants were then placed in a greenhouse at from 20° to 22° C. and from 75 to 80% relative humidity. The extent of fungus development was determined after 10 days.

In this test, active ingredients nos. 13, 14, 15, 19, 31, 32, 36, 41, 42, 45, 57, 59 and 60 had a very good action.

EXAMPLE C

Action on bacteria

To determine the action on bacteria, 5 ml of increasing dilutions of the active ingredients was added to 5 ml of doubly concentrated nutrient broth in sterile test tubes, and mixed. The tubes were then inoculated by adding one drop of a 16-hour old broth culture (diluted 1:10) of the bacteria species Staphylococcus aureus and Escherichia coli, and incubated for 24 hours at 37° C. After this time, samples were transferred from the tubes to bacteria nutrient media which were then also incubated for 24 hours at 37° C.

In this test, active ingredients nos. 53, 54, 55, 58 and 60 had a good action.

EXAMPLE D

Action on Candida albicans and Oidium lactis

To determine the action on fungi, the active ingredients are added, in amounts of 100, 50, 25, 12, 6 and 3 parts per million parts of solution, to a nutrient solution ideally suited for promoting the growth of the fungi Candida albicans and Oidium lactis. 10 ml of the mixture of nutrient solution and active ingredient was introduced into sterile test tubes and inoculated with one drop of a spore suspension containing $10^6$ conidia or cells. After 120 hours' incubation, samples were taken from those tubes exhibiting no visible fungus growth and transferred to fungus nutrient media.

In this test, active ingredients nos. 54, 55, 58 and 60 had a good action.

We claim:

1. A dibenzofuran derivative of the formula

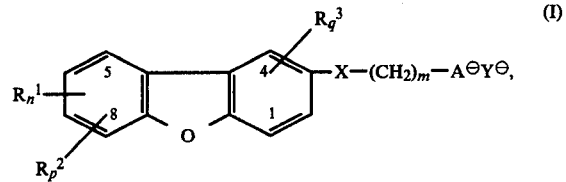

where $R^1$, $R^2$ and $R^3$ are identical or different and each is halogen, unsubstituted or halogen-substituted alkyl or alkoxy of 1 to 4 carbon atoms, cyano or nitro, n, p and q are 0, 1, 2 or 3, X is oxygen or sulfur, m is 2, 3 or 4, $A^\oplus$ is quinuclidinium or pyrrolizidinium, or $-N^\oplus R^4R^5R^6$, where $R^4$, $R^5$ and $R^6$ are identical or different and each independently of one another is alkyl, alkenyl or alkynyl of not more than 6 carbon atoms, cycloalkyl of not more than 12 carbon atoms or cycloalkenyl of not more than 7 carbon atoms, which acyclic and cyclic radicals may be substituted by halogen, cyano, alkoxy of 1 to 4 carbon atoms or dialkylamino, where alkyl is of 1 to 4 carbon atoms, or is aralkyl which is unsubstituted or substituted by fluorine, chlorine, bromine, alkyl, alkenyl or alkoxy of not more than 4 carbon atoms, trifluoromethyl, nitro, cyano or alkoxycarbonyl of not more than 5 carbon atoms, or $R^5$ together with $R^6$ is part of a 5-, 6- or 7-membered saturated heterocyclic ring which contains from 1 to 3 hetero-atoms selected from the group consisting of nitrogen, oxygen and sulfur and may be substituted by methyl or ethyl, and $Y^\ominus$ is the anion of any desired nonphytotoxic acid HY.

2. A dibenzofuran derivative of the formula I as claimed in claim 1, wherein $R^1$ is halogen, alkyl or alkoxy of 1 to 4 carbon atoms, trifluoromethyl or nitro, n is 1, 2 or 3, p and q are 0, X is oxygen, m is 2, 3 or 4, A is $-N^{\oplus}R^4R^5R^6$, $R^4$, $R^5$ and $R^6$ being identical or different and each independently of one another being unsubstituted or halogen-substituted alkyl of 1 to 5 carbon atoms or cycloalkyl of 3 to 6 carbon atoms, and $Y^{\ominus}$ is the anion of any desired non-phytotoxic acid HY.

3. A dibenzofuran derivative of the formula I as claimed in claim 1, wherein $R^1$ is halogen, alkyl or alkoxy of 1 to 4 carbon atoms, trifluoromethyl or nitro, n is 1, p and q are 0, X is oxygen, m is 2, 3 or 4, A is $-N^{\oplus}R^4R^5R^6$, $R^4$ being unsubstituted benzyl or benzyl substituted by fluorine, chlorine, bromine, trifluoromethyl, nitro or by alkyl of 1 to 4 carbon atoms, and $R^5$ and $R^6$ being part of an unsubstituted or methyl- or ethyl-substituted 5-, 6- or 7-membered saturated heterocyclic ring which contains from 1 to 3 hetero-atoms, and $Y^{\ominus}$ is the anion of any desired non-phytotoxic acid HY.

4. N-Benzyl-N-2-(7-chlorodibenzofuran-3-oxy)-ethylpiperidinium chloride.

5. N-(2,4-Dichlorobenzyl)-N-2-(7-chlorodibenzofuran-3-oxy)-ethylpiperidinium chloride.

6. A fungicidal agent containing inert additives and from 0.1 to 95% by weight of a dibenzofuran derivative of the formula I as defined in claim 1.

7. A process for combating fungi, wherein from 0.1 to 5 kg/hectare of a dibenzofuran derivative of the formula I as defined in claim 1 is allowed to act on the fungi, or on areas, plants or seeds threatened by fungus attack.

* * * * *